United States Patent [19]

Gifford

[11] Patent Number: 4,889,109

[45] Date of Patent: Dec. 26, 1989

[54] KNEE SEPARATION CUSHION

[76] Inventor: Koger B. Gifford, P.O. Box 9804, Long Beach, Calif. 90810

[21] Appl. No.: 306,582

[22] Filed: Feb. 6, 1989

[51] Int. Cl.⁴ ............................................... A61F 5/00
[52] U.S. Cl. .................................. 128/80 A; 128/80 R
[58] Field of Search ................ 128/80 A, 80 R, 80 B, 128/168, 882, 87 C; 5/437

[56] References Cited

U.S. PATENT DOCUMENTS

| | | | |
|---|---|---|---|
| 2,887,151 | 5/1959 | Springer | 128/68 |
| 3,339,544 | 9/1967 | Kravitz | 128/80 |
| 3,421,163 | 1/1969 | Stoughton | 128/68 |
| 3,505,994 | 4/1970 | Smith | 128/80 R |
| 3,532,336 | 10/1970 | Baker | 269/328 |
| 3,604,023 | 9/1971 | Lynch | 5/327 |
| 3,769,969 | 11/1973 | Nezik | 128/68 |
| 3,842,453 | 10/1974 | Redfield | 128/68 |
| 3,946,451 | 3/1976 | Spann | 5/327 |
| 4,135,504 | 1/1979 | Spann | 128/80 |
| 4,177,806 | 12/1979 | Griffin | 128/132 |
| 4,210,317 | 7/1980 | Spann et al. | 269/328 |
| 4,270,235 | 6/1981 | Gutmann | 128/68 |
| 4,327,714 | 5/1982 | Spann | 128/80 |
| 4,392,489 | 7/1983 | Wagner | 128/80 |
| 4,441,221 | 4/1984 | Enste et al. | 5/431 |
| 4,471,952 | 9/1984 | Spann | 269/328 |
| 4,502,170 | 3/1985 | Morrow | 128/80 R |
| 4,584,730 | 4/1986 | Rajan | 5/431 |
| 4,624,021 | 11/1986 | Hofstetter | 5/431 |
| 4,736,477 | 4/1988 | Moore | 5/443 |
| 4,805,605 | 2/1989 | Glassman | 128/80 A |

Primary Examiner—William Pieprz
Assistant Examiner—Huong Q. Pham
Attorney, Agent, or Firm—Fulwider, Patton, Lee & Utecht

[57] ABSTRACT

A cushion having a knee separating portion. The cushion is shaped with a arcuate top surface, and the knee separating portion is in the form of a projection centrally located in the arcuate top surface. Straps are provided to fasten the pillow in place.

9 Claims, 2 Drawing Sheets

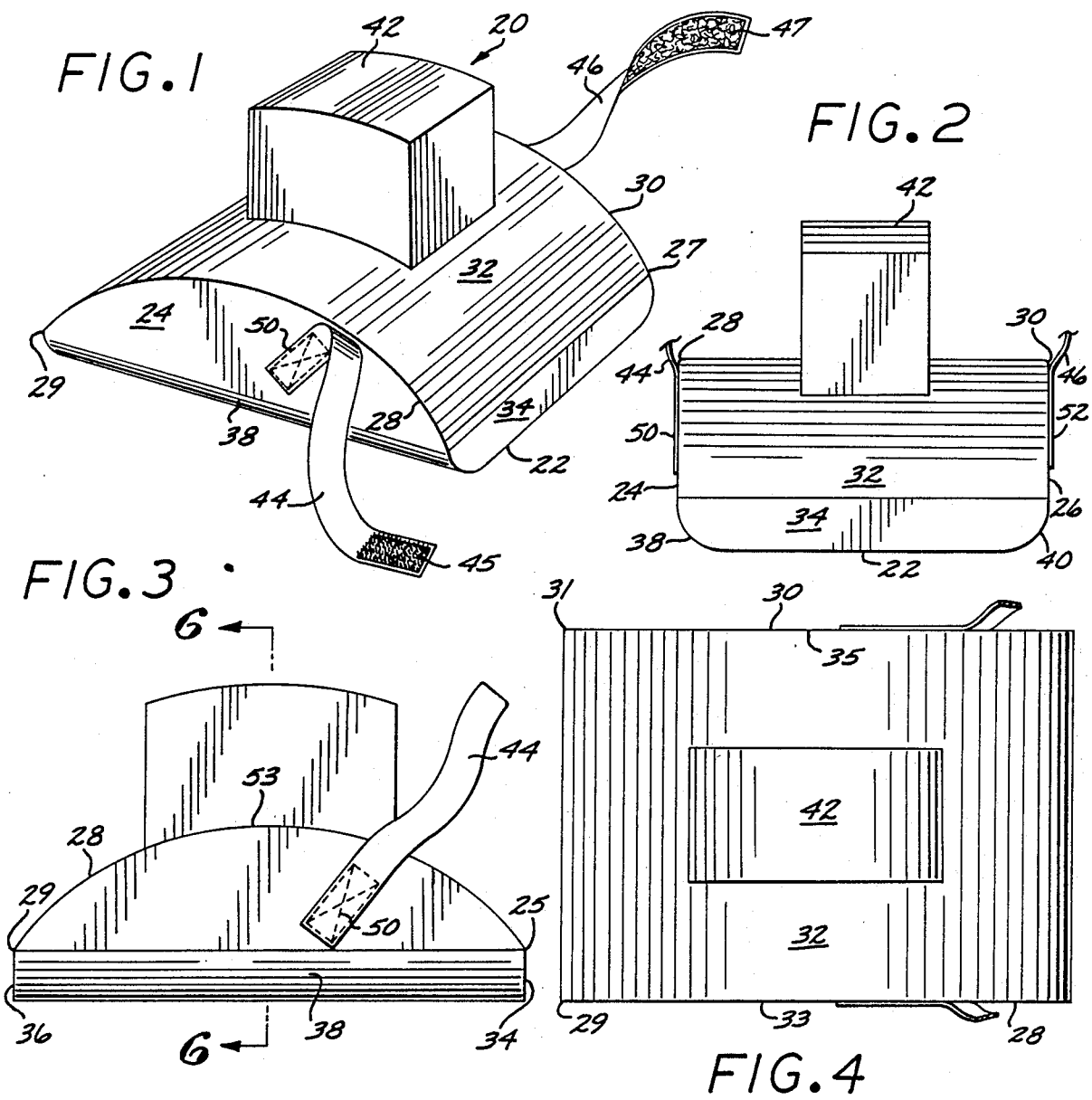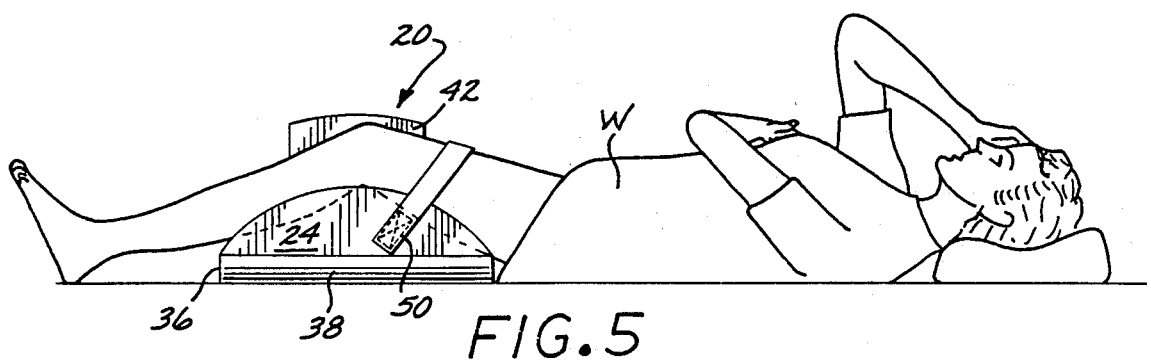

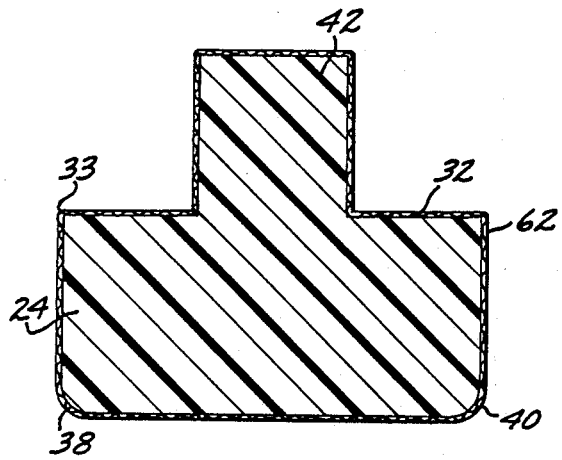
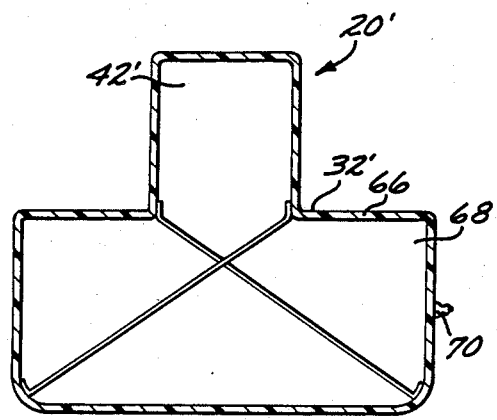
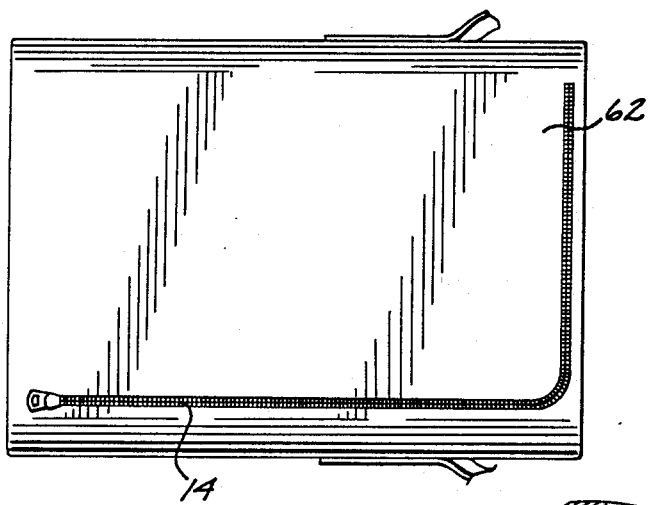
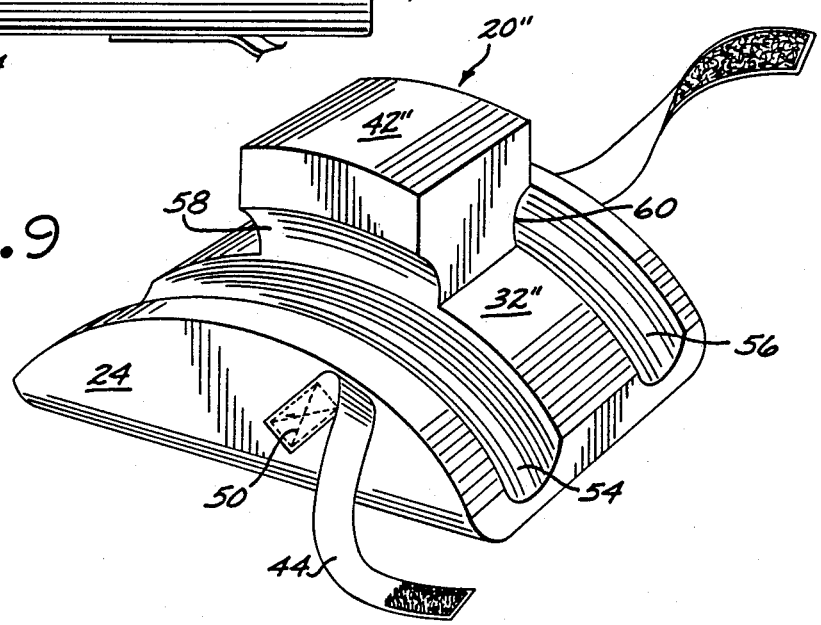

KNEE SEPARATION CUSHION

BACKGROUND OF THE INVENTION

1. Field of the Invention

This invention relates to a support cushion, and in particular to a cushion capable of supporting the legs of a human wearer in a bent at the knee position while simultaneously separating the legs and cushioning the knees from one another.

2. Description of the Prior Art

It is often necessary for persons, especially those recovering from back injuries or surgery, to recline with their legs bent at the knees and with their legs apart. In certain situations, particularly in patients subjected to prolonged confinement to bed, serious problems, including decubitus ulceration, serious nerve irritation and other painful or debilitating injuries may result if the knees are not cushioned and held apart.

Where a person is required to cushion his knees from one another and maintain his legs in a spread-apart position obtaining restful sleep may be a problem. Doctors have long recommended that patients needing to maintain their legs in this position place a pillow between their knees. However, use of a conventional pillow for this purpose has proved difficult and unwieldy since any motion may act to dislodge the pillow. This is especially a problem if the person is asleep and therefore unaware that the pillow needs to be replaced. Similarly, if a nurse or other person moves a patient having a pillow between his legs to cushion his knees and dislodges the pillow, replacement may be awkward and difficult.

Certain prior art cushions, such as the knee pillow designed to be strapped to the inside of one knee as that described in U.S. Pat. No. 4,736,477 to Moore, provides for some cushioning between the knees. While undoubtedly effective for the purpose for which they were designed, such pillows do not provide adequate positioning or support for a prone or sleeping individual. They also do not maintain the legs in a spread apart position.

Likewise, leg positioning cushions such as those shown in U.S. Pat. No. 4,135,504 to Spann are known in the prior art. However, while such cushions may be adequate for functioning as abduction pillows to position a patient for surgery, as described in that patent, they are not comfortable or convenient for home use. Furthermore, they are not suited for use during restful sleep, since, unlike this invention, they resist movements such as rolling over.

Accordingly, it is an object of the present invention to provide a leg cushion which simultaneously supports the legs of a supine wearer in a bent at the knee position while maintaining a cushion between the knees of said wearer.

Another object of this invention is to provide a cushion to maintain the legs of a wearer in a spread apart position.

Another important object of this invention is to provide a cushion between the knees of a wearer which is not dislodged by restless movement during sleep.

Another important object of this invention is to provide a cushion between the knees of a wearer which does not resist rolling over by a wearer.

Still another important object of this invention is to provide a cushion between the knees convenient for home use.

SUMMARY OF THE INVENTION

The present invention provides a novel cushion which supports and pads the legs of a supine wearer in a bent at the knee position while providing a cushion between the knees of the wearer. Straps across the legs of the wearer prevent the cushion from being displaced should the wearer move as when he rolls over. Furthermore, a rounded transition area between the base and side walls of the cushion allows the wearer to roll onto his side with relative ease while retaining the cushion positioned between his knees.

Other objects and features of the invention will become apparent from consideration of the following description taken in connection with the accompanying drawings.

BRIEF DESCRIPTION OF THE DRAWINGS

FIG. 1 is a perspective drawing of a first embodiment of a knee separation cushion of the present invention;

FIG. 2 is an end view of a first embodiment of the knee separation of the present invention;

FIG. 3 is a side view of the knee separation cushion of a first embodiment of the present invention;

FIG. 4 is a top plan view of a first embodiment of the knee separation cushion of the present invention;

FIG. 5 is a side view, in reduced scale, of a first embodiment of the knee separation cushion of the present invention shown in use by a supine wearer;

FIG. 6 is a cross-section of the cushion of a first embodiment of the knee separation cushion of the present invention taken along line 6-6 of FIG. 3;

FIG. 7 is a cross-section taken along the lines of 6—6 in FIG. 3 of a second embodiment of the present invention taking the form of an inflatable cushion;

FIG. 8 is a bottom view of the base of a first embodiment of the cushion of the present invention having a cloth-like cover;

FIG. 9 is a perspective view of a third embodiment of the knee separation cushion of the present invention showing leg receiving troughs in the arcuate top surface thereof.

DESCRIPTION OF PREFERRED EMBODIMENTS

The drawings illustrate three embodiments of the knee separation cushion of this invention: a resilient solid material cushion such as close foam cell material 20; an inflatable cushion 20'; and a cushion 20" having leg receiving troughs thereon.

The knee separation cushion 20 of the first embodiment is made with a pillow having a generally planar base 22 on which the cushion rests when upright. The base may be, for example, about 20 inches long and 14.5 inches wide.

Side walls 24, 26 extend upward from the lateral edge of the base 22. The top edges 28, 30 of the side walls 24,26 define the lateral edge of the top arcuate surface 32. The top edges 28, 30, curve upward from the base from a low point 25, 27 for example 2 inches directly above the corner of the base to a high point 33, 35 for example 7.5 inches above the center of the side edge of the base, and then back toward the base to a second low point 29, 31, for example two inches above the other corner of the base.

A central projection 42 extends upwardly from the arcuate top surface 32. The central projection 42 is not coextensive in width or length with the arcuate top surface 32. Rather it may be, for example, only 5 inches wide and 20 inches long. It is firmly affixed to the arcuate top surface 32 so that forces, especially lateral forces such as caused by knees pressing against it, will not dislocate it.

Thus, the cylindrical surface, when the pillow is oriented on its base as is shown in FIG. 5, forms leg receiving channels on opposite sides of the central spacer post 42 to angle arcuately forwardly and downwardly from the apex area 53 of such cylindrical section to terminate at the cephalad forward end of the pillow thus defining upwardly and forwardly facing surfaces 41 and 43 which are receivable under the ham string area of the wearer's thighs as shown in FIG. 5. Such cylindrical surface further forms rearward of the apex or peak surface 53 the downwardly and rearwardly curved surface to form the upwardly and rearwardly facing surfaces 45 and 46 disposed on the opposite sides of the separator post 42 for supporting the calves of the wearer as viewed in FIG. 5.

Side straps 44, 46 are affixed to the side walls 24, 26 for strapping over the arcuate top surface and snugly holding the legs 48 of a wearer W between the straps and the arcuate top surface. This may clearly be seen in FIG. 5. The attachment area 52 of the straps 44, 46 to the side walls is resilient, so that when the straps 44, 46 are fastened across the thighs of a wearer W they apply tension to the strap to snugly capture the thighs between the fastened straps and the arcuate top surface 32. The straps may be provided on their unattached ends with contact fasteners 45, 47 such as (VELCRO).

Referring to FIG. 6, the pillow itself may be made of a resilient foam material such as a closed cell foam material commonly known in the art for making cushions. It may be covered with a cushion cover 62 for durability and cleanliness. The strap attachment areas, 50, 52, may be on the cover 62 rather than on the pillow itself. The cover over the base may be provided with a zipper 64. When the zipper is open, the cushion cover may be removed from around the pillow for cleaning or replacement of the cover or of the pillow.

A second embodiment, illustrated in FIG. 7, takes the form of a knee separation cushion 20' configured as described above but fabricated of material rendering it inflatable. Thus cushion 20' is hollow and airtight, composed of an airtight skin 66 which defines an inflatable compartment 68. When air under pressure is put into compartment 68 through inlet valve 70, the cushion assumes the shape shown in FIG. 7, including an arcuate top surface 32' and a central projection 42'. When inlet valve 70 is opened and air is allowed to escape, the cushion 20' may be deflated for ease of storage and transportation.

Referring to FIG. 9, a third embodiment of the knee separation cushion 20" includes an arcuate top surface 32" having channels therein 54, 56 for receipt of the legs of the wearer. The central projection 42" may be configured with indentations 58, 60 for receipt of the wearer's legs.

In practice, a wearer W lies supine and places his legs over the arcuate surfaces of the cushion and on either side of the central projection 42. He then fastens the straps snugly over his thighs trapping his thighs between the arcuate top surface and the fastened straps. This effectively affixes the cushioned central projection between his knees, holding his legs apart and cushioning his knees from contact with each other. When the wearer, either consciously or unconsciously, rolls or moves, the cushion remains affixed in place. For example, if the wearer rolls from his back to his left side, the cushion remains attached between his legs with the central projection cushioning his knees and keeping his legs spread apart. The curved transition area between the flat base and the flat left sidewall facilitates the rolling of the cushion from an upright position to its left side, and allows the wearer to roll without undue resistance from the cushion. Because the cushion remains strapped to the wearer, repositioning the cushion after such a movement is not necessary and the wearer need not consciously retain the cushion in place.

Although one specific embodiment of the invention has been described and illustrated, the invention is not to be limited to the specific forms and arrangements of parts so described and illustrated, and various modification and changes thereto can be made without departing from the scope and spirit of the invention. Within the scope of the appended claims, therefore, the invention may be practiced otherwise than as specifically described and illustrated herein.

I claim:

1. A leg support and knee separation cushion for fitting under the legs of a wearer to separate the knees of a wearer and maintain them elevated from a bed surface and comprising:

a pillow having a front end and a rear end and right and left side walls, said pillow being formed with a downwardly facing planar bottom surface extending from said front end to said rear end for engaging said bed surface, a top surface being curved upwardly from said front and rear ends respectively to form respective, laterally spaced apart forwardly and upwardly facing ham string support surfaces and rearwardly and upwardly facing calf support surfaces, said pillow being further formed between said respective ham string and calf support surfaces with respective peak areas for nesting behind the respective knees of such wearer;

a cushioning post defining a separation extension projecting upwardly from said pillow between said peak areas for maintaining such knees spaced apart; and a pair of holding straps connected on their respective one ends to said respective left and right side walls of said cushion, back of said straps having a free end including fastening means for releasably connecting the free ends thereof together to secure said cushion to such legs whereby said cushion may be positioned behind the knees of such wearer lying in a supine position on such bed with said bottom surface flat against such bed surface and such knees elevated by said peak surfaces, said straps fastened to secure said cushion to such legs such that said pillow will be secured thereto in the event of rolling over of said patient to a side position to thereby maintain such knees spaced apart.

2. A leg support and knee separation cushion comprising:

a pillow having a front end and a rear end and right and left side walls, said pillow being formed with a downwardly facing planar bottom surface extending from said front end to said rear end for engaging said bed surface, a top surface being curved upwardly from said front and rear ends respectively to form respective, laterally spaced apart forwardly and upwardly facing ham string support surfaces and rearwardly and upwardly facing calf support surfaces, said pillow being further formed between said respective ham string and calf support surfaces with respective peak areas for nesting behind the respective knees of such wearer;

a cushioning post defining a separation extension projecting upwardly from said pillow between said peak areas for maintaining such knees spaced apart; and a cover for closely covering the surface of said pillow, said cover having a left side surface which immediately overlays the left side wall and a right side surface which immediately overlays the right side wall of said pillow; and a pair of holding straps connected on their respective one ends to said respective left and right side surfaces of said cover, each of said straps having a free end including fastening means for releasably connecting the free ends thereof together to secure said cushion having said cover to such legs whereby said cushion may be positioned behind the knees of such wearer lying in a supine position on such bed with said bottom surface flat against such bed surface and such knees elevated by said peak surfaces, said straps fastened to secure said cushion to such legs such that said pillow will be secured thereto in the event of rolling over of said patient to a side position to thereby maintain such knees spaced apart.

3. A pillow as in claim 2, further comprising;

a left transition surface and a right transition surface, said left transition surface located between said base and said left side wall, said left transition surface extending outwardly and upwardly from said base to connect with said left side wall and extending between said front end and said rear end, said right transition surface located between said base and said right side wall, said right transition surface extending upwardly and outwardly from said base to said right side wall and extending between said front end and said rear end.

4. A leg support and knee separation cushion as in claim 2, wherein said pillow is inflatable.

5. A leg support and knee separation cushion as in claim 4 further having an inlet valve for introduction and removal of fluid material for inflation and deflation of said leg support and knee separation cushion.

6. A leg support and knee separation cushion as in claim 3 wherein:

said separation extension has a width dimension, said width dimension being approximately that of a human leg;

said base is rectangular, having two parallel lengths and two parallel widths, said lengths being slightly shorter than the length of a human leg, said widths being approximately the width of three human legs.

7. A knee separator cushion according to claim 8 wherein:

said pillow is in the form of a sector of a cylinder with the surface defined by the chord thereof corresponding in size with said bottom surface and defining a rectangle about 20 inches long and 14½ inches wide.

8. A leg support and knee separation cushion as in claim 1, wherein said pillow is inflatable.

9. A leg support and knee separation cushion as in claim 8 having an inlet valve for introduction and removal of fluid material for inflation and deflation of such leg support and knee separation cushion.

* * * * *